United States Patent [19]

Baskas et al.

[11] 4,159,570
[45] Jul. 3, 1979

[54] DISPOSABLE MIXING SYRINGE

[75] Inventors: Morris J. Baskas, New Rochelle; Sidney I. Berger, New York, both of N.Y.

[73] Assignee: Dentipressions Incorporated, New York, N.Y.

[21] Appl. No.: 847,270

[22] Filed: Oct. 31, 1977

[51] Int. Cl.² .......................... A61C 7/00; A61M 5/00; B65D 25/08
[52] U.S. Cl. .................................. 32/66; 128/218 M; 206/222
[58] Field of Search .............................. 32/17, 60, 66; 128/218 M; 215/6; 222/386; 220/89 A, 89 R; 206/222

[56] References Cited
U.S. PATENT DOCUMENTS

| 3,340,873 | 9/1967 | Solowey | 128/218 M |
|---|---|---|---|
| 3,448,750 | 6/1969 | Parks | 220/89 A |
| 3,537,605 | 1/1969 | Solowey | 128/218 M |
| 3,595,439 | 7/1971 | Newby et al. | 128/218 M |
| 3,760,503 | 9/1973 | Baskas | 32/17 |
| 3,815,878 | 6/1974 | Baskas et al. | 128/218 M |
| 3,858,853 | 1/1975 | Rausch et al. | 222/386 |
| 4,059,109 | 11/1977 | Tischlinger | 128/218 M |

Primary Examiner—Louis G. Mancene
Assistant Examiner—Michael J. Foycik

[57] ABSTRACT

A disposable mixing syringe especially adapted for dental use is described. It comprises a barrel of uniform inside diameter divided by a fixed diaphragm into upper and lower chambers for receiving respectively first and second components of a mixture to be formed and terminating in a nozzle having a small orifice. A removable closure seals the opposite barrel end. Inserting a mixing tool through the diaphragm allows rapid mixing of the constituents, after which a suitable plunger is provided to expel the contents through the orifice.

13 Claims, 5 Drawing Figures

U.S. Patent     Jul. 3, 1979     4,159,570
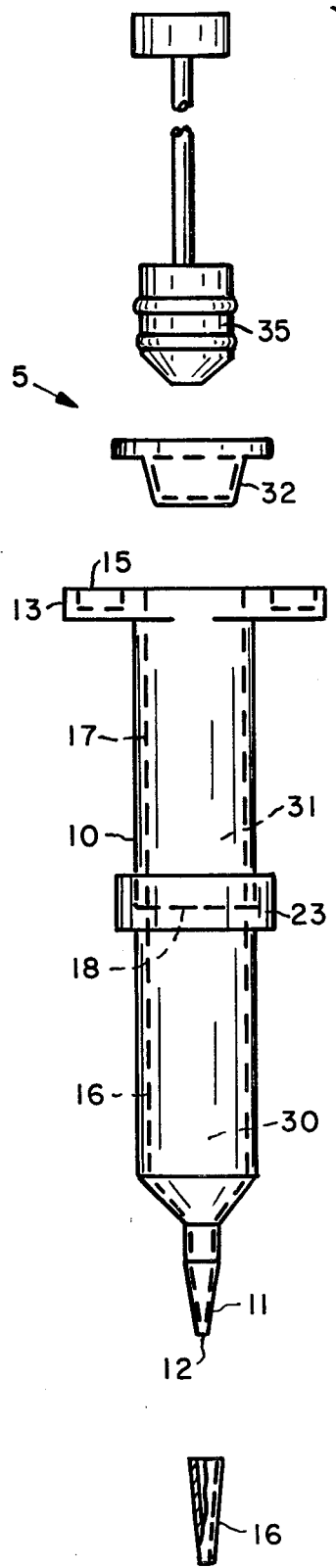
Fig. 1
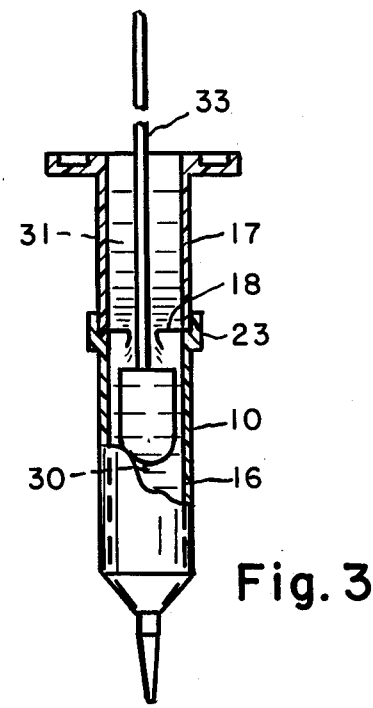
Fig. 3
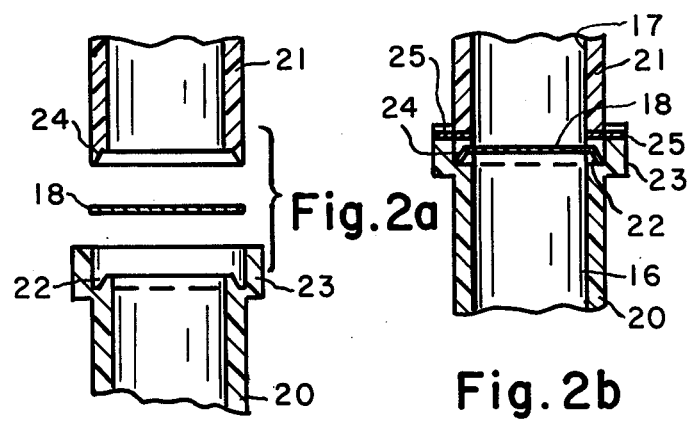
Fig. 2a
Fig. 2b
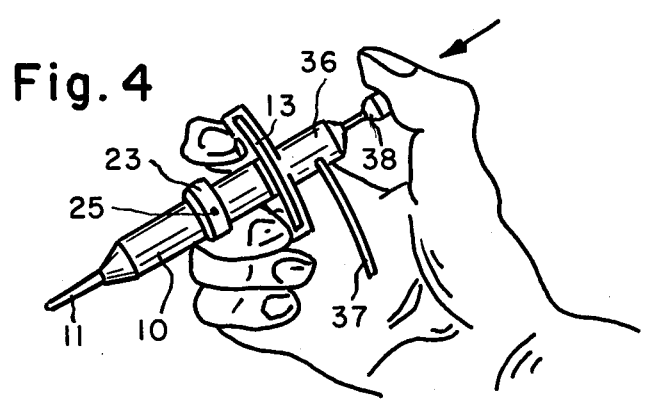
Fig. 4

DISPOSABLE MIXING SYRINGE

This invention relates to a combination mixing syringe and disposable dispensing device especially adapted for dental use.

Known dental impression techniques conventionally employ a tray filled with an impression material such as hydrocolloid which is pressed onto the patient's jaw to form an impression of the teeth and gum. After hardening, the hydrocolloid is removed from the mouth and employed as a negative mold to form a positive casting by investing same with for example a suitable dental stone. This technique is cumbersome and has many disadvantages. It has been proposed to use a hardenable silicone in place of the hydrocolloid. However, to produce a hardenable silicone requires mixing of a basic silicone resin with a suitable catalyst. This is now accomplished by the dentist himself removing a suitable amount of the resin from a tube supplied by a supplier, adding to that a correct proportion of the catalyst also taken from a tube available from the supplier, mixing these ingredients on a suitable slab, transferring the mixture to a syringe, and then applying the mixture to the patient's teeth. This procedure also is quite cumbersome and time-consuming and requires the dentist to take the necessary precautions to ensure that the mixture is carefully proportioned and properly applied to the patient. Also, the syringe must then be cleansed for the next application.

Reference is made to a commonly assigned issued U.S. Pat. No. 3,760,503, whose contents are hereby incorporated herein. That patent describes a disposable mixing syringe suitable for this purpose, wherein a first component of a mixture to be formed is located within a syringe barrel, and a second component of a mixture to be formed is located within a sealed removable insert package seated in the open end of the syringe barrel opposite the dispensing end. A drawback of this known syringe is that the size of the insert chamber is much smaller than the size of the syringe barrel, with the result that the patented syringe is not well suited for forming mixtures of generally equal proportions of two components. A further drawback is that the insert package required separate fabrication, and this increased the expense of the assembly.

A principal object of the invention is a device of the type described in which desired proportions of a multi-component mixture are preestablished though maintained separately, and by which they can be readily mixed, and the mixture then readily applied in an appropriate manner to an object to be coated.

This and other objects and advantages of the invention as will appear herein after are achieved, in accordance with the invention, by a disposable syringe comprising a barrel of uniform inside diameter having at one end an exiting orifice and at the opposite end an opening. A diaphragm is mounted within the barrel dividing same into plural chambers, in each of which is provided a component of the mixture to be formed. The diaphragm is constituted of a thin flexible film of material which can be readily punctured and when punctured will not separate or split into loose pieces. The open end of the barrel is sealed with a closure. Operation is similar to that described in the patented device. The closure is removed, a mixing tool inserted to puncture the diaphragm and then mix the components, after which the tool is removed and a plunger inserted to expel the mix through the exiting orifice.

Among the advantages of the novel device of the invention are low-cost manufacture, pre-measured proportions of the ingredients ensuring the optimum mixture composition, disposability due to low cost, and minimum time expenditure by the user.

One exemplary embodiment of the invention will now be described in greater detail with reference to the accompanying drawing, wherein:

FIG. 1 is an exploded elevational view of the various parts of one form of combination syringe and mixing device of the invention;

FIG. 2a and 2b are respectively, cross-sectional exploded and assembled views illustrating mounting of the diaphragm separator within the syringe;

FIG. 3 is a cross-section of the syringe showing how it is used;

FIG. 4 is a side view of the syringe fitted with means for pressure dispensing of the mixture.

One form of the invention is shown in exploded view for clarity in FIG. 1. It comprises a disposable syringe 5 comprising a generally cylindrical barrel 10 tapering down at its bottom end to a flexible nozzle 11 having a small exiting orifice 12. It may be constituted of any suitable plastic resin. The upper end is formed with an enlarged flange 13 by which the syringe may be manually held or secured to a pressure-generating device. The top surface 15 of the flange is generally flat. The nozzle end 11 can be closed off with a removal cap 16 which may be held on the nozzle by a friction fit.

In this preferred embodiment, the mixture to be formed will contain two components of equal size. Thus, the syringe barrel 10 is divided into two chambers 16 and 17 by means of a diaphragm 18 which is mounted within the barrel. As is illustrated in FIG. 1, the inside diameter of the upper and lower barrel halves is the same, for engagement and cooperation with a common plunger to be later described.

The mounting of the diaphragm 18 is illustrated in FIG. 2. Before assembly, the barrel is divided into two halves 20 and 21, only the adjoining ends of which are shown in FIG. 2. The adjoining ends are provided with a mating annular tongue and annular groove as illustrated in FIG. 2a. The groove 22 is formed in the lower barrel post 20 at an enlarged end shown at 23. The tongue 24 is formed at the upper barrel part 21. The diaphragm 18 is shown between the disassembled barrel parts 20 and 21 in FIG. 2a.

To assemble, first the lower barrel part 20 is filled with the first fluid component 30 of the mixture to be formed. Next, the diaphragm 18 is seated over the top opening of the lower barrel part 20. The diameter of the diaphragm 18 is chosen to overlap the groove 22. Next, the upper barrel part 21 is brought down and the tongue 24 mated as by pushing with the groove 22, thus mechanically locking the diaphragm 18 to the assembled barrel halves, as shown in FIG. 2b. The two barrel parts are then permanently joined together by any suitable means. For example, a suitable adhesive may be provided between the mating barrel parts to glue the two together, with the diaphragm separator 18 in place. Alternatively, the diaphragm 18 may be glued in the groove 22 of the lower barrel part, and subsequently, the upper barrel part glued to the lower barrel part. As a further alternative, the mating barrel ends can be configured to form a bayonet-type joint, thus mechanically joining the barrel halves by rotation.

It is preferred however to weld the two barrel parts together along their sides mechanically locking the diaphragm 18 in between. A preferred method is by ultrasonic welding at several spaced points around the periphery of the enlarged ring portion 23. With polypropylene for the barrel material, this has been accomplished using commercially available ultrasonic welding equipment by spot-welding the barrel sides together at three points around the periphery, illustrated at 25 in FIG. 2b. This spot-welding satisfactorily holds the two barrel halves together keeping the diaphragm 18 tightly locked within the tongue and groove joint, and forming the lower chamber 16 containing the first component 30, and the upper chamber 17 which will house the second component 31.

The diaphragm material is chosen to provide adequate isolation between the two chambers 16 and 17, yet resist fracturing or splintering into small pieces when punctured during use. A preferred material for the diaphragm 18 is thin MYLAR plastic. MYLAR foils of 4 mils thick have been satisfactorily used. Other similar thin, flexible plastic foils should also be suitable. Aluminum foil has not performed satisfactorily because when punctured pieces can be broken off and lodge in the mixture to be formed, which may be undesirable. The foil should be sufficiently flexible that the plunger used to eject the mix, which plunger is usually of rubber, will readily pass over the foil parts that remain along the barrel interior after puncturing.

After the barrel halves have been assembled as shown in FIG. 2b, the second fluid component 31 of the mix is introduced into the upper chamber 17. Then a suitable closure 32 is provided at the top which fits tightly within the opening of the thus assembled syringe to seal off the contents. In the form shown, the closure 32 is a small cup, but other constructions, such as a foil glued over the top, or a cork, should also be suitable.

In use, the user removes the closure 32 and merely inserts a spatula 33 or like paddle type of tool as shown in FIG. 3 through the open end of the syringe 10 and down into the barrel causing puncturing of the diaphragm 18 allowing the second component 31 to flow into the lower chamber and come into contact therein with the first component 30. The user then manipulates the spatula 33 to thoroughly mix the two components. For this purpose, the tool may have a cylindrical shank which can be inserted into a conventional handpiece to power rotate the tool allowing rapid mixing of the two constituents. This need only take some 10-20 seconds. Next, the user removes the mixing tool 33.

To expel the mixture, a suitable plunger 35 of elastic material is then inserted in the open end of the syringe 10, and after removal of the cap 16, pressing of the plunger will expel the mixture in a uniform bead from the orifice 12. In this way, the user can apply a thin coating or bead of a desired mixture where wanted. Afterwards, the syringe 10 may be disposed of.

For more uniform mixture dispensing, a pressurized air system can be coupled to the syringe. This is illustrated in FIG. 4. After the mixture has been formed and the mixing tool removed, a shankless plunger 35 is inserted in the barrel open end, and then a suitable air-valve 36 attached to the open end of the barrel using its flange 13 to hold the air-valve in place. A supply of pressurized air is coupled by way of a suitable conduit 37 to the air-valve. On pressing the air-valve actuator 38, air under controlled pressure pushes the plunger 35 uniformly into the barrel expelling the mixture from the orifice.

As has been mentioned above, the invention is generally applicable to any two-component mixture which requires component separation up until the moment of use, and then intimate contact of the components in preferred proportions in a device enabling rapid and controlled dispensing where desired. Typically, the components will be of the type that undergo a chemical reaction when brought into contact with one another. In the dental field, generally the components will form plastic resin compositions, frequently involving a change of form or state. Thus, both components may be liquids, which when contacted harden to form a solid. An example is the so-called silicone resins, of the fast-setting type, which requires mixing of a resin component and catalyst hardener. A reaction occurs immediately causing setting in some cases in as short as 3 minutes. Thus, the mixed resin has to be applied quickly. Any of the commercially available silicones, which are primarily organosilicon compositions, can be used. The invention is best adapted for those mixtures requiring substantially equal proportions of two constituents, since each chamber can be adapted to have the same volume. Examples are epoxy adhesives, rubber materials, and dental impression materials. For those mixtures where, for instance, the component proportions are in a ratio of 1:4, the syringe construction can be modified by relocating the joint further up the syringe to increase the volume of the lower chamber 16 and reduce the volume of the upper chamber 17 to the desired values. Three-component mixtures can also be readily formed by replacing the closure 32 with a sealed insert as described in the previously referred to U.S. Pat. No. 3,760,503, and including the third component in the insert package. Puncturing and mixing would take place in the same manner as for the two component embodiment.

While the principles of the invention have now been made clear in several illustrative embodiments, there will be immediately obvious to those skilled in the art many modifications in structure, arrangement proportions, the elements, materials, and components, used in the practice of the invention, and otherwise, which are particularly adapted for specific environments and operating requirements, without departing from those principles. The appended claims are therefore intended to cover and embrace any such modifications, within the limits only of the true spirit and scope of the invention.

What is claimed is:

1. A disposable syringe and mixing assembly comprising a syringe barrel of uniform inside diameter having an exiting orifice at one end and an opening at the opposite end, a diaphragm seated within said barrel and separating the interior of the barrel into a lower chamber at said one end and an upper chamber at the opposite end, a first component of a mixture to be formed within the lower chamber, a second component of the mixture to be formed within the upper chamber, said diaphragm being constituted wholly of thin flexible foil sheet material that is readily punctured but without fracturing into separate pieces, said barrel being divided into upper and lower parts joined at said diphragm location, one of said barrel parts having at the junction an annular groove, the other of said barrel parts having at the junction an annular projecting tongue fitted within and mating with said annular groove, said foil sheet being seated between the tongue and groove and being mechanically locked thereby into position within the barrel, and a removable closure at said opposite end of the barrel, removal of the closure allowing insertion of a mixing tool for puncturing of the diaphragm and mixing of the two components within the syringe barrel.

2. A disposable syringe and mixing assembly as claimed in claim 1, and further comprising separable plunger means for insertion into the barrel for engaging the barrel walls for expelling the mixture through the exiting orifice.

3. A disposable syringe and mixing assembly as claimed in claim 2, and further comprising a separable paddle mixing tool for puncturing the diaphragm and for mixing of the first and second components.

4. A disposable syringe and mixing assembly as claimed in claim 1, wherein the diaphragm is of MYLAR.

5. A disposable syringe and mixing assembly as claimed in claim 3, wherein the exiting orifice is small and the opposite end opening is larger.

6. A disposable syringe and mixing assembly as claimed in claim 1, wherein welds connect together the barrel upper and lower parts.

7. A disposable syringe and mixing assembly as claimed in claim 1, wherein the diaphragm is glued to the barrel.

8. A disposable syringe and mixing assembly as claimed in claim 6, wherein the barrel is of plastic material, and the welds are ultrasonic spot welds.

9. A disposable syringe and mixing assembly as claimed in claim 3, wherein the mixing tool is a paddle whose width is smaller than the inside barrel diameter.

10. A disposable syringe and mixing assembly as claimed in claim 1, wherein the removable closure comprises a small cup seated in the opposite open end of the barrel.

11. A disposable syringe and mixing assembly comprising a syringe barrel of uniform inside diameter having an exiting orifice at one end and an opening at the opposite end, a diaphragm seated within said barrel and separating the interior of the barrel into a lower chamber at said one end and an upper chamber at the opposite end, a first component of a mixture to be formed within the lower chamber, a second component of the mixture to be formed within the upper chamber, said diaphragm being constituted wholly of thin flexible foil sheet material that is readily punctured but without fracturing into separate pieces, said barrel being divided into upper and lower parts joined at said diaphragm location, one of said barrel parts having at the junction an annular groove for receiving the other of said barrel parts, said foil sheet being seated between the barrel parts and within the groove and being mechanically locked thereby into position within the barrel, and a removable puncturable closure cup containing a third component of the mixture to be formed at said opposite end of the barrel, the assembly allowing insertion of a mixing tool for puncturing of the cup and of the diaphragm and mixing of the three components within the syringe barrel.

12. A disposable syringe and mixing assembly as claimed in claim 11, and further comprising separable plunger means for insertion into the barrel for engaging the barrel walls for expelling the mixture through the exiting orifice.

13. A disposable syringe and mixing assembly as claimed in claim 12, and further comprising a separable paddletype mixing tool for puncturing the cup and diaphragm and for mixing of the first, second, and third components.

* * * * *